(12) United States Patent
Koopman

(10) Patent No.: US 9,089,584 B2
(45) Date of Patent: Jul. 28, 2015

(54) TREATMENT OF TISSUE ADHESION

(75) Inventor: Jacob Koopman, Leiden (NL)

(73) Assignee: PROFIBRIX B.V., Leiden (NL)

(*) Notice: Subject to any disclaimer, the term of this patent is extended or adjusted under 35 U.S.C. 154(b) by 0 days.

(21) Appl. No.: 13/321,954

(22) PCT Filed: May 28, 2010

(86) PCT No.: PCT/EP2010/057478
§ 371 (c)(1),
(2), (4) Date: Nov. 22, 2011

(87) PCT Pub. No.: WO2010/136589
PCT Pub. Date: Dec. 2, 2010

(65) Prior Publication Data
US 2012/0064165 A1  Mar. 15, 2012

(30) Foreign Application Priority Data
May 28, 2009 (GB) .................................. 0909136.4

(51) Int. Cl.
A61K 9/14 (2006.01)
A61K 31/7016 (2006.01)
A61K 9/00 (2006.01)
A61K 31/715 (2006.01)
A61K 38/36 (2006.01)
A61K 38/48 (2006.01)
A61K 45/06 (2006.01)

(52) U.S. Cl.
CPC ........... A61K 31/7016 (2013.01); A61K 9/0014 (2013.01); A61K 9/145 (2013.01); A61K 31/715 (2013.01); A61K 38/363 (2013.01); A61K 38/4833 (2013.01); A61K 45/06 (2013.01)

(58) Field of Classification Search
CPC .. A61K 9/0014; A61K 9/145; A61K 31/7016
USPC ...................................... 424/489, 94; 514/13
See application file for complete search history.

(56) References Cited

U.S. PATENT DOCUMENTS

| 5,702,715 A | 12/1997 | Nikolaychik et al. |
| 5,906,924 A | 5/1999 | Mandai et al. |
| 6,113,948 A * | 9/2000 | Heath et al. ..................... 424/499 |
| 6,632,457 B1 * | 10/2003 | Sawhney ....................... 424/501 |
| 2002/0001584 A1 | 1/2002 | Metzner et al. |
| 2003/0181917 A1 | 9/2003 | Gertner |
| 2005/0123588 A1 * | 6/2005 | Zhu et al. ....................... 424/443 |
| 2006/0104970 A1 | 5/2006 | Margel et al. |
| 2007/0276505 A1 | 11/2007 | Barry et al. |
| 2008/0033331 A1 * | 2/2008 | MacPhee et al. ............... 602/50 |
| 2008/0033333 A1 | 2/2008 | MacPhee et al. |
| 2009/0098061 A1 | 4/2009 | Suzuki et al. |

FOREIGN PATENT DOCUMENTS

| CN | 1364889 A | 8/2002 |
| CN | 1454667 A | 11/2003 |
| CN | 1617735 A | 5/2005 |
| EP | 1157706 A2 | 11/2001 |
| EP | 1905443 A1 | 4/2008 |
| JP | 3258723 A | 11/1991 |
| WO | 9744015 | 11/1997 |
| WO | 0024436 | 5/2000 |
| WO | 03047530 A2 | 6/2003 |
| WO | 2005021011 A1 | 3/2005 |
| WO | 2005089472 A2 | 9/2005 |
| WO | 2006012541 A2 | 2/2006 |
| WO | 2009046194 A2 | 4/2009 |
| WO | 2010002435 A2 | 1/2010 |
| WO | 2010136588 A2 | 12/2010 |

OTHER PUBLICATIONS

Kilburn et al., Title: Organization and mobility of water in amorphous and crystalline trehalose; Nature Materials 5, 632-635 (2006), published online: Jul. 9, 2006 by Nature Publishing Group.*
Maggos, C.; BioCentury Title: "ProFibrix: Hemostatic sprinkles", BioCentury, Mar. 26, 2007; p. A15.*
Dias et al., Title: Chitin and chitosan: characteristics, uses and production current perspectives, Journal of Biotechnology and Biodiversity, vol. 4, Issue 3, 2013, Abstract.*
Cesaro et al.; Title: Water interplay in trehalose polymorphism; Food Chemistry, vol. 108, pp. 1318-1328; published 2008.*
Notification Concerning Transmittal and International Preliminary Report on Patentability dated Dec. 8, 2011 from corresponding International Application No. PCT/EP2010/057478 filed May 28, 2010.
Cannon et al., Rate of Epithelial Regeneration, Annals of Surgery, Jan. 1943, pp. 85-92.
Klemm, Enhanced Healing of Skin Wounds in Dogs with Systemically and Locally Administered Drugs, Specialia, 1967, pp. 55-57.
Yi Xiaodong et al., Experimental study on long-term effect of employing Fibrin Sealant to prevent post-surgical epidurar scar adhesions, Clinical Surgery, Feb. 2005, vol. 13, Issue 2, pp. 101-102.

* cited by examiner

Primary Examiner — Ali Soroush
Assistant Examiner — Yanzhi Zhang
(74) Attorney, Agent, or Firm — Young Basile

(57) ABSTRACT

Dry powder compositions are useful in the treatment or prevention of tissue adhesions during or after surgery or during wound therapy. The dry powder compositions may contain trehalose. The dry powder compositions may be fibrin sealant compositions comprising fibrinogen and/or thrombin.

12 Claims, No Drawings

TREATMENT OF TISSUE ADHESION

TECHNICAL FIELD

This invention relates to the use of a dry powder composition, or fibrin sealant in powder form, for prevention or reduction of tissue adhesions, e.g. post-operative adhesions.

BACKGROUND

Post-surgical adhesions are of significant clinical and medico-economic relevance, since, for example, post-surgical adhesions cause about 40% of cases of chronic pelvic pain and approximately 20% of cases of infertility. Indeed, adhesions cannot be prevented without employing adjuvant therapy, and every minute trauma may result in their formation.

Many materials have been found to have a positive effect on reduction of surgical adhesions, such as sodium hyaluronate/carboxymethylcellulose films, collagen films and gels, as well as fibrin glues.

EP1905443 describes the administration of a solution containing trehalose for the reduction and/or prevention of adhesion during or after surgery.

Lee et al (*Japanese Journal of Veterinary Anesthesia & Surgery*, Vol. 40, pp. 19-26 (2009) disclose the reduction of experimentally-induced post-surgical adhesions of internal organs after ovariohysterectomy in a rabbit model by spraying solutions of sodium carboxymethylcellulose in conjunction with trehalose solutions onto the surface of visceral organs.

The effect of liquid fibrin glues on anti-adhesion is somewhat controversial. Many reports implied the possible prevention of post-surgical adhesions using such liquid fibrin glues (e.g. Brands et al., Chirurg 61 (1990): 22-26; Lindenberg et al., Ann. Chir. Gynecol. 73 (1984): 11-13; De Iaco et al., Fertility and Sterility 62 (2) (94): 400-404; Takeuchi et al., J. Am. Assoc. Gynecol. Laparosc. 3 (4) (1996): 575-579; Martin-Cartez et al., Surg Today, 2008, 38(2): 135-40). However, other studies found no significant effect in preventing adhesion formation or the effect on reproduction after adhesion complications post-surgery (see e.g. Marana et al., Gynecol. Obstet. Invest. 41 (1996): 199-202 and Gauwerky et al., Arch. Gynecol. Obstet. 247 (1990): 161-166).

Recent comparative tests indicated that collagen gels, collagen films and sodium hyaluronate/carboxymethylcellulose films effectively reduced adhesion formation, whereas the effect of liquid fibrin glues on adhesion formation was similar to the control.

It is therefore an object of the present invention to provide a method and compositions for efficiently reducing or preventing tissue adhesion in a patient.

SUMMARY

In a first aspect of the invention, there is provided a method for reducing or preventing tissue adhesions in a patient during or after surgery or during wound therapy, said method comprising topically administering an effective amount of a trehalose-containing dry powder to exposed or separated tissues during said surgery or wound therapy. In a related aspect, the invention provides a pharmaceutical composition in the form of a trehalose-containing dry powder, for use in the treatment or prevention of tissue adhesions during or after surgery or during wound therapy.

Surprisingly, it was discovered that post-surgical adhesions are reduced or prevented when such trehalose-containing dry powder compositions were employed as an adjunct in surgery.

In a second aspect of the invention, there is provided a method for reducing or preventing tissue adhesions in a patient during or after surgery or during wound therapy, said method comprising topically administering an effective amount of a dry powder fibrin sealant to exposed or separated tissues during said surgery or wound therapy. In a related aspect, the invention provides a pharmaceutical composition in the form of a dry powder fibrin sealant, for use in the treatment or prevention of tissue adhesions during or after surgery or during wound therapy.

In a third aspect of the invention, there is provided a method for reducing or preventing tissue adhesions in a patient during or after surgery or during wound therapy, said method comprising topically administering an effective amount of a dry powder fibrin sealant composition to exposed or separated tissues during said surgery or wound therapy, wherein said dry powder fibrin sealant composition comprises a mixture of first microparticles that comprise fibrinogen and second microparticles that comprise thrombin. In a related aspect, the invention provides a pharmaceutical composition in the form of a dry powder fibrin sealant comprising a mixture of first microparticles that comprise fibrinogen and second microparticles that comprise thrombin, for use in the treatment or prevention of tissue adhesions during or after surgery or during wound therapy.

In a fourth aspect of the invention, there is provided a method for reducing or preventing tissue adhesions in a patient during or after surgery or during wound therapy, said method comprising topically administering an effective amount of a dry powder fibrin sealant composition to exposed or separated tissues during said surgery or wound therapy, wherein said dry powder fibrin sealant composition comprises a mixture of first microparticles that comprise fibrinogen, second microparticles that comprise thrombin, and further comprising additive material. In a related aspect, the invention provides a pharmaceutical composition in the form of a dry powder fibrin sealant comprising a mixture of first microparticles that comprise fibrinogen and second microparticles that comprise thrombin, and further comprising additive material, for use in the treatment or prevention of tissue adhesions during or after surgery or during wound therapy.

In a fifth aspect of the invention, there is provided a method for reducing or preventing tissue adhesions in a patient during or after surgery or during wound therapy, said method comprising topically administering an effective amount of a dry powder fibrin sealant composition to exposed or separated tissues during said surgery or wound therapy, wherein said dry powder fibrin sealant composition comprises a mixture of first microparticles that comprise fibrinogen and trehalose and second microparticles that comprise thrombin and trehalose. In a related aspect, the invention provides a pharmaceutical composition in the form of a dry powder fibrin sealant comprising a first microparticles that comprise fibrinogen and trehalose and second microparticles that comprise thrombin and trehalose, for use in the treatment or prevention of tissue adhesions during or after surgery or during wound therapy.

In a sixth aspect of the invention, there is provided a method for reducing or preventing tissue adhesions in a patient during or after surgery or during wound therapy, said method comprising topically administering an effective amount of a dry powder fibrin sealant composition to exposed or separated tissues during said surgery or wound therapy, wherein said dry powder fibrin sealant composition comprises a mixture of first microparticles that comprise fibrinogen and trehalose, second microparticles that comprise thrombin and trehalose, and further comprising additive material. In a related aspect, the invention provides a pharmaceutical composition in the form of a dry powder fibrin sealant comprising a mixture of first microparticles that comprise fibrinogen and trehalose, second microparticles that comprise thrombin and trehalose, and further comprising additive material, for use in the treatment or prevention of tissue adhesions during or after surgery or during wound therapy.

In a seventh aspect of the invention, there is provided a method for reducing or preventing tissue adhesions in a patient during or after surgery, said method comprising topically administering an effective amount of a dry powder fibrin sealant composition to exposed or separated tissues during said surgery or wound therapy, wherein said dry powder fibrin sealant composition comprises a mixture of first microparticles that comprise fibrinogen, second microparticles that comprise thrombin, and further comprising additive material, wherein the additive material comprises a polysaccharide or chemically-modified polysaccharide. In a related aspect, the invention provides a pharmaceutical composition in the form of a dry powder fibrin sealant comprising a mixture of first microparticles that comprise fibrinogen, second microparticles that comprise thrombin, and further comprising additive material, wherein the additive material comprises a polysaccharide or chemically-modified polysaccharide, for use in the treatment or prevention of tissue adhesions during or after surgery or during wound therapy.

In an eighth aspect, the invention provides a kit comprising a composition according to the invention, optionally with a dispensing device.

In a ninth aspect, the invention provides the use of the composition of the invention, or the components thereof, in the manufacture of a medicament for the prevention, treatment and/or alleviation of tissue adhesions.

WO97/44015 describes a dry powder fibrin sealant based on micro-particles of fibrinogen and thrombin. Further optimized formulations of these microparticle compositions are described in co-pending application U.S. patent Ser. No. 12/636,718, which is herein incorporated by reference. In the Example of this US application the components are prepared by separately spray-drying fibrinogen with trehalose and thrombin with trehalose. Each product has a predominant particle size of up to 50 µm diameter. The fibrin sealant, a blend of these components, has been demonstrated to be an easy-to-use, stable and efficacious topical hemostat. The product can be used immediately, without reconstitution. On contact with aqueous fluid such as blood, the exposed active thrombin converts the exposed fibrinogen into insoluble fibrin polymers.

DETAILED DESCRIPTION

The first aspect of the invention is based on the discovery of a new use of trehalose when present in a powder composition. The method according to the present invention is efficient in reducing or preventing tissue adhesions in a patient by administering a trehalose-containing dry powder composition to a surgical site or a wound. The adhesions to be reduced or prevented in a patient with the method according to the present invention may be adhesions to or between organs, parts of organs or other tissues. Adhesions may also be defined as abnormal attachments between organs and/or other tissues.

In other embodiments of the invention, topically administering an effective amount of a dry powder fibrin sealant to exposed or separated tissues during surgery or wound therapy reduces or prevents adhesions in a patient.

In other embodiments of the invention, topically administering an effective amount of a dry powder fibrin sealant to exposed or separated tissues during surgery or wound therapy, reduces or prevents adhesions in a patient, wherein said dry powder fibrin sealant composition comprises a mixture of first microparticles that comprise fibrinogen and/or second microparticles that comprise thrombin.

It is known that fibrin plays a role in adhesion reduction or prevention. Without wising to be bound by theory, it is believed that the reaction of the thrombin and fibrinogen in a powder form, whereby the dry powder dissolves in small quantities of blood or plasma, etc. results in the formation of a denser layer of fibrin than that found when using a liquid fibrin sealant or fibrin glue. This dense barrier of fibrin enhances the anti-adhesion effect.

Since adhesion often inhibits normal movement of tissues, including organs, it is therefore considered to be a serious complication after surgery. For instance, adhesions following tendon surgery may result in dyskinesia. Furthermore, organ adhesion after intra-abdominal surgery may cause complications such as ileus, pain and sterility.

Where a dry powder thrombin preparation and/or a dry powder fibrinogen preparation are used, they may be provided as a set, preferably together with suitable administration devices.

The adhesions which are preferably reduced or prevented may result from gynecological reproductive surgery, abdominal surgery, spinal and laparoscopic surgery but the composition can be widely used in not only thoracotomy or laparotomy but also hepatic surgery, neurosurgical procedures, orthopedic procedures relating to tendon or ligament, etc, as well as in wound therapy.

An "effective amount" of a preparation according to the present invention is any amount which is able to reduce or prevent adhesion formation in a patient significantly as compared to a control group without such an administration.

According to a further aspect, the present invention relates to the use of a dry powder fibrin sealant/composition comprising an effective amount of trehalose, homologs, analogs, or derivatives thereof, for producing a preparation for reduction or prevention of adhesion formation in a patient during or after surgery.

The composition may also include at least one or more polysaccharides, mucopolysaccharides, salts of polysaccharides, and salts of mucopolysaccharides having lubricating properties. Chemically-modified derivatives of mucopolysaccharides, such as benzylated hyauronic acid and the like, may also be present in the composition.

In this specification, "tissue" refers to a body tissue such as skin, organ, muscle, nerve, cartilage, bone. The dry powder for tissue adhesion prevention of the invention can be applied to various animals, mammalian species, most particularly in humans.

Trehalose is widely present in nature including animals, vegetables and microorganisms. It is contained in yeasts such as bakers' yeast and brewers' yeast, and it is a saccharide often found in foods.

Suitable forms or isoforms of trehalose which may be employed in the invention include hydrated crystalline trehalose, anhydrous crystalline trehalose, anhydrous amorphous trehalose, α,α-trehalose, α,β-trehalose (neo-trehalose), β,β-trehalose (iso-trehalose), or mixtures thereof.

Polysaccharides containing carboxyl groups, carboxymethylcellulose, carboxymethylchitin, carboxymethylchitosan, carboxymethylstarch, alginic acid, pectin, carboxymethyldextran etc. may also be present. Mucopolysaccharides which may also be present include hyaluronic acid (HA), heparin, heparin sulfate, and chondroitin sulfate. As water-soluble salts, sodium salts, alkali metal salts or alkali earth metal salts can be used. Combinations may also be included, such as carboxymethylcellulose and chemically-modified hyaluronic acid.

Respective fibrinogen-containing and thrombin-containing soluble microparticles comprising trehalose can be formulated and blended together, in stable, dry form. This formulation can be subsequently employed as a fibrin sealant that is useful in wound therapy and surgical repair.

The fibrinogen and the thrombin may be isolated from blood from human donors or be made by recombinant DNA technology in cultured cells or transgenic animals or plants.

The fibrinogen or thrombin may be full-length or any active fragment thereof. The content of fibrinogen in the microparticles containing it may be about 0.1 to 50% w/w, preferably about 0.5 to 20 w/w, as well as 5 to 10% w/w, or about 6.5% w/w. The content of thrombin in the microparticles containing it may be about 10 to 20,000 IU/g, preferably about 25 to 1000 IU/g, or 100 to 500 IU/g.

The active-containing microparticles and/or additive material may be solid or hollow, such as in the case of microcapsules. Microparticles comprising fibrinogen or thrombin may be prepared by methods known in the art, for example as described in WO 92/18164, WO 96/09814, WO 96/18388 or WO 97/44015. These spray-drying and associated particle manipulation processes enable the production of soluble protein microcapsules with defined size distribution, for example of up to 50 μm in diameter. For example, as described in those documents, the microparticles may be produced reproducibly, e.g. with 90% or more (by volume) up to 30 μm, e.g. 10 to 20 μm, in size. Readily-flowing agglomerates of these particles may be made in situ by adjusting the air flow configuration in the spray-dryer to counter-current, or arranging multiple atomizers into a "forced primary agglomeration" set-up, as would be appreciated by persons skilled in the art. Such agglomerates may be 50 to 1000 μm or 100 to 500 μm, or 125 to 250 μm in diameter. Respective fibrinogen-containing and thrombin-containing soluble microparticles can be formulated and blended together within a spray-drying apparatus by the use of a multi-nozzle atomizer, as described in WO03/037303.

Although the preferred method of preparation of the dry powder formulation includes spray drying, other drying techniques may also be used to prepare the dry powder formulation. Suitable methods are known in the art and include fluidized bed drying and freeze-drying, with subsequent micronization, or spray-freeze drying. Microparticles may be sterilized, if necessary or desired, using techniques known in the art.

Microparticles of the invention are preferably prepared by spray-drying. Typically, a 2-fluid nozzle is used which utilizes compressed air during the atomization process; this results in the production of hollow microparticles. The maximum particle size of microparticles (X50, as measured by Sympatec) that can be manufactured using this atomization system on the Niro Mobile Minor spray dryer is ~30 μm. Preferred X50 values for the microparticles of the invention are between 5 and 50 μm, most preferably between 10 and 20 μm. The microparticles may be hollow or solid.

The first or second microparticles of the invention may be prepared by spray-drying a solution of the active component, e.g. fibrinogen or thrombin, with a carrier material such as a saccharide. An alternative procedure comprises co-spray-drying, in which the active component and another wall-forming material are formulated and spray-dried, to give microparticles in which the active component is incorporated into the particle.

In an embodiment of the invention, the dry powder composition comprises trehalose with fibrinogen suitable for use in the prevention or reduction of adhesions during or after surgery. The fibrinogen and trehalose may be combined together in a composite microparticle by spray-drying as described herein, or any other technique known to the skilled person.

In an embodiment of the invention, separate microparticles comprising fibrinogen and separate microparticles comprising thrombin are blended with trehalose to produce a dry powder composition suitable for use in the prevention or reduction of adhesions during or after surgery.

In an embodiment of the invention, solid or hollow fibrinogen-containing microparticles are blended with solid or hollow thrombin-containing microparticles and with an additive material as described herein, in any sequence which produces a homogenous blend. Such blending can be carried out using low shear or high-shear blending, or any other technique known to persons skilled in the art.

The fibrinogen or thrombin may be full-length or any active fragment thereof. Fragments are known; see Coller et al, J. Clin. Invest. 89:546-555 (1992). Fibrinogen raw material may be a frozen solution, though lyophilized powder which requires reconstitution prior to spray-drying may be used.

Suitable other proteins may be naturally occurring or be made by recombinant DNA technology in cultured cells or transgenic animals or plants. The fibrinogen or thrombin may be full-length or any active fragment thereof. They may act as "wall-forming materials", as described in WO92/18164, where various examples are given. A preferred material is HSA (human serum albumin). For example, fibrinogen is spray-dried alone or in the presence of varying amounts of excipients such as HSA (e.g. fibrinogen: HSA ratios of 1:1, 1:3, 3:1) and trehalose. Other suitable substitutes for HSA include surfactants, such as Tween 20, Tween 80, Poloxamer 407 or Poloxamer 188. Calcium ions, e.g. as calcium chloride, may be incorporated in the thrombin feedstock. Alternatively, calcium chloride may be added to the microparticles after processing.

In certain embodiments of the invention, the additive material used in the invention typically has an average particle size of from 10 to 1000 μm, or 100 to 500 μm, or 125 to 250 μm or possibly, for example, 10 to 40 μm. The additive may comprise one material or may be a mixture of materials. Such additive material may act as a carrier and/or diluent for the active materials.

Additive materials that may be present in the form of particles having particle sizes of the order set out in the preceding paragraph include such additives as biocompatible water-absorbent and/or water-swellable materials, polysaccharides, porous and/or hollow materials.

In such cases, the additive material may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, by weight of the composition, or any range or value between.

Typically, the composition in such cases will comprise at least 1%, or at least 5% or at least 10% w/w of additive material, and up to 60%, up to 70% or up to 80% of additive material. Thus, the additive may be present at a level of from 1% (or 5% or 10%) to 80%, or from 1% (or 5% or 10%) to 70%, or from 1% (or 5% or 10%) to 60% w/w of the composition.

In other embodiments of the invention, the additive material typically has an average particle size of from about 10 nm to 10 μm, and may comprise one material or may be a mixture of materials.

In other embodiments of the invention, the additive material is not a solid soluble material.

Various materials may be present as additive particles, for enhancing flow and wettability, etc. Preferably the material is insoluble or very slowly soluble. Such materials may include dextran polymers, e.g. Sephadex, which are available in different particle sizes, starches including hetastarch, pullulan derivatives, hyaluronic acid and esters thereof. Cellulose products such as microcrystalline cellulose (Avicel range), methylcellulose, carboxymethyl cellulose, microfine cellulose or hydroxy propyl cellulose, hydroxypropylmethylcellulose, hydroxypropylcellulose, low-substituted hydroxypropyl cellulose, hydroxyethylcellulose and other materials such as cross-linked polyvinyl pyrrolidone (PVP), may be used singly or in admixture. Also, suitable additive materials acting as carriers include polyethylene glycol (PEG), preferably having a molecular weight of about 1000; polyvinylpyrrolidone (PVP), preferably having an average molecular weight of about 50,000; Poly(acrylic acid), polyacrylamide, poly vinyl alcohol (PVA), Poly(methylvinylether co-maleic anhydride), Poly(ethyleneoxide), and dextran, typically having an average molecular weight of about 40,000.

Other suitable additive materials may be soluble such as saccharides including mono- and di-saccharides, including lactose, lactose monohydrate, anhydrous lactose, sucrose, maltose, anhydrous maltose, fructose, maltitol, sorbitol, xylitol, mannitol or trehalose itself when the carrier material in the fibrinogen and/or thrombin containing microparticles does not comprise trehalose. Suitable oligosaccharides include dextrin, dextran sulphate, pullulan, hyaluronic acid and salts thereof, either alone or in combination.

In other embodiments of the invention, the additive is a highly porous and highly soluble interwoven filamentary crystal, e.g. of sorbitol and/or mannitol. Such materials are sold under the name PARTECK SI and PARTECK M (Merck KGaA, Darmstadt, Germany). These grades have a high adsorption capacity and so are suitable for blending with the dry powder fibrin sealant powder composition of the invention, to produce a novel powder which reduces dusting, and enhances wettability, solubilization and performance of the dry powder fibrin sealant, by allowing blood to soak through the applied powder bed and thus avoid clotting at the powder interface alone.

Microparticles of the invention may be sterilized, if necessary or desired. Sterile processing, electron beam irradiation, γ-irradiation and ethylene oxide are examples of suitable techniques.

The additive materials may be present in the composition of the invention as single components or in combination and may be present in the feedstock or added to either spray-dried thrombin or fibrinogen before blending together, or added to the final blend and subjected to further blending. Such blending can be carried out using low shear or high-shear blending, mechano-chemical bonding, hybridization or any other technique known to persons skilled in the art.

Although the components of the microparticles in a fibrin sealant of the invention are preferably water-soluble, and the microparticles are preferably obtained by spray-drying a suitable solution, the microparticles that are obtainable may be free-flowing, discrete and substantially dry or anhydrous, with a residual moisture content preferably no greater than about 8% w/w or about 5% w/w, most preferably no greater than 3% w/w. This means that the compounds of fibrin sealant in accordance with this invention are not activated until they are wetted, e.g. by coming into contact with liquid at a wound site. The active components may therefore be delivered as a dry mixture, although separate application of the different microparticles is also envisaged. The active-containing microparticles are preferably amorphous or in the form of a glass at room temperature (e.g. 25° C.) so as to stabilize the entrapped protein as well as to present the active in such a rapidly-soluble state. Preferably the active-containing microparticle composition exhibits a glass transition temperature of greater than about 25° C., or about 30° C., or about 40° C., or about 50° C., or more, as measured by Differential Scanning calorimetry or modulated Differential Scanning calorimetry. The additive material may also be amorphous or in the form of a glass at room temperature (e.g. 25° C.) so as to be in a rapidly-soluble state. Preferably the additive material exhibits a glass transition temperature of greater than about 25° C., or about 30° C., or about 40° C., or about 50° C., as measured by Differential Scanning calorimetry or modulated Differential Scanning calorimetry. Such glassy compositions enable the composition to be stored at ambient or room temperature, e.g. 25° C., for extended periods of time, for example greater than 3 months or greater than 6 months, without significant losses in activity.

The additive material may also be in a crystalline or amorphous state but may also be free-flowing, discrete and substantially anhydrous, with a residual moisture content preferably no greater than 5% w/w, most preferably no greater than 3% w/w.

The powder composition may be applied using the powder delivery device of co-pending application PCT/GB2009/051714, herein incorporated by reference.

The invention will now be described, by way of illustration only, with reference to the following Examples.

Example 1

This study investigated the effect a powder according to the invention in a porcine liver wound model. Tissue response to the application of the fibrin sealant comprising trehalose was also examined and tissue response and haemostasis using said fibrin sealant was also compared with Tisseel—a commercially available, liquid application fibrin sealant.

Study Materials

Dry powder fibrin sealant was prepared, as described in co-pending application U.S. Ser. No. 12/636,718. In brief, Fibrinogen (ZLB, Marburg, Germany) and trehalose (Pfanstiehl, Waukegan, Ill., USA) hollow spherical particles were prepared. The concentration of fibrinogen in the particles is 12% (w/w).

Thrombin (SNBTS, Glasgow, Scotland) and trehalose were spray dried to obtain hollow particles. Thrombin was present in a concentration of 1000 IU per gram of particles. The particles were blended in a 1:1 ratio; the resulting powder has a 6% w/w concentration of fibrinogen and 500 IU/gram of powder. This blend is referred to as the Inventive Powder.

The Inventive Powder was prepared and made ready for application whilst Tisseel was bought in and prepared, as per supplier's instructions.

Animals

One female, Large White/Landrace crossbred pig was used at 45 kg bodyweight.

Experimental Protocol

The Inventive Powder and Tisseel were applied to liver biopsy wound sites.

Surgical Protocol

A midline laparotomy was performed, using diathermy, to expose the ventral surface of the liver. The dorsal hepatic ligament between liver and diaphragm was transected to allow distal movement of the liver. The left lateral lobe of the liver was elevated and exteriorized onto wet swabs. A 10 mm punch biopsy tool was adjusted to cut 4 mm in depth. Six punch biopsies were performed, one at a time, on the parenchymal surface of the left lobe of the liver allowing at least 3 cm of normal tissue between the edges of each biopsy site. The punch biopsy tissue was removed to leave a 10 mm×4 mm crater defect in the surface of the liver lobe. As soon as the tissue was removed, pre-weighed swabs were used to collect blood from the site at the rate of one per minute. Swabs were weighed to establish the site bleed rate for three minutes. The site was then treated as according to the experimental protocol and swab collection continued for 5 minutes or until there was haemostasis. Once 6 sites had been created and treated on the left lobe, this was replaced into its original position within the peritoneal cavity and the central lobe elevated and exteriorized onto wet swabs. Identical procedures were carried out for 5 sites on the central lobe of the liver. Once all surgical procedures were complete and satisfactory haemostasis achieved for all biopsy sites, 500 ml of sterile saline was flushed over the liver surface into the peritoneal cavity. The peritoneum and internal muscle layer of the laparotomy was closed with 2/0 Vicryl on a half round atraumatic needle. The external muscle and skin incision of the laparotomy was closed with 2/0 Prolene on a half round cutting needle. The closed laparotomy site was treated with Cicatrin powder and oversprayed with Opsite. The subject was recovered from anaesthetic, extubated and returned to the animal accommodation. The subject was monitored for any adverse clinical signs for 14 days.

Termination

The subject was pre-medicated and anaesthetized. A midline laparotomy incision was started at the level of the iliac fossa and extended proximally to reveal the liver surface and the operative sites. Macroscopic observations were recorded. The left lateral and central lobes of the liver were removed complete.

Results

Clinical

No adverse clinical signs were noted during the post-operative monitoring period, all physiology appeared normal during this time.

Macroscopy

At terminal laparotomy there were no adhesions present between the internal aspect of the peritoneal suture line and the underlying bowel, omentum or spleen. However, there were adhesions from the tips of the liver lobes to the ipsilateral peritoneum which extended over the whole of the liver surfaces which had been manipulated during the operative procedures. The central lobe and the left lateral lobe were adhered together along the junction where the central lobe was overlying the left lateral lobe. Most of these adhesions, apart from the region of the central lobe tip, were all easily freed by gentle finger pressure. There were two regions, which appeared to coincide with a treated biopsy site, which were more difficult to separate, one of these areas was so heavily adhered that the liver was torn during separation. Other regions coinciding with treated biopsy sites were subjectively easier to separate than the surrounding liver parenchymal areas. There was also one piece of what appeared to be treatment material which was dislodged from its attachment during the adhesion separation. All wound sites appeared well closed and were characterized by small depressions in the parenchymal surface of the liver lobes. There did not appear to be significant inflammation of the biopsy defect rims and there was no macroscopic evidence of treatment material present on the liver surface. There were areas of opaque filmy material over three of the sites which appeared to be fibrous and attached to the biopsy defect. On the internal surface of the diaphragm there were two areas which showed an amount of what appeared to be treatment material attached to the diaphragm and surrounded with opaque, filmy, fibrous tissue.

It was surprisingly found that there were differences in adhesion between Tisseel and the Inventive Powder. In all Tisseel treated sites there were tenacious adhesions between the infill material and the overlying diaphragm or liver lobe. These were so tenacious at one site that the separation caused the wound site to lose some of the infill material and re-haemorrhage. Contrastingly, in all but one of the sites treated with Inventive Powder, while there were adhesions between the unoperated liver surface adjacent to the treatment site and the overlying diaphragm, there were no adhesions between the treatment site itself and the overlying diaphragm even in one case which showed increased inflammatory reaction.

Example 2

Materials and Methods

Rabbits were used for this study due to published data and in-house experience. Inventive Powder from Example 1 and Seprafilm (ex Genzyme), a commercially-available anti-adhesion product, were compared with untreated tissue used as control. All materials tested were stored and applied according to manufacturer's instructions.

Surgical Procedure

Surgery was performed using aseptic technique with the surgeon wearing cap, mask and sterile gloves. The instruments were sterilized by autoclaving in the first instance but subsequently cleaned in chlorhexidine in alcohol between animals.

- An abdominal full-thickness midline incision was made and the wound edges retracted with tissue forceps.
- The uterine horn of one side was located and elevated from the cavity for easy access.
- A rectangular template measuring 26 mm×3 mm was positioned on the horn and the surface scraped ten times with a purpose-made serrated metal scraper (5 times in each direction) to create an abrasion.

A template measuring 24 mm×3 mm was then positioned on the ipsilateral peritoneal wall and an abrasion created as described above.

In the case of untreated control sites, the two wounds were approximated and secured with two 5/0 prolene sutures, one at each end of the abraded area. In the case of treated sites, the test articles were applied between the abraded sites before approximation and securing.

A similar procedure was then performed on the opposite horn.

When complete, the abdominal muscle was closed with interrupted 2/0 vicryl sutures whilst the skin was closed using first, a continuous subcuticular 3/0 silk suture followed by interrupted 2/0 silk sutures.

Termination

At 14 days post surgery, all subjects were euthanized using an overdose of barbiturate. Both operative sites from each subject were excised, together with adjacent associated tissues, and these samples were placed into 10% neutral buffered formal saline to fix.

Results

In animals treated with the Inventive Powder, there was a distinct separation of the two abraded surfaces such that these surfaces were healing independent of one another. This was also true of the Seprafilm treated samples. From the histology results (not shown) it was found that the Inventive Powder may reduce or prevent post-surgical adhesions.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

The invention claimed is:

1. A method comprising:
reducing or preventing tissue adhesion formation between organs or between organs and other tissues in a subject after a surgical procedure, wherein the surgical procedure is selected from a group consisting of gynecological reproductive surgery, abdominal surgery, spinal and laparoscopic surgery, hepatic surgery, neurosurgical procedures and orthopedic procedures, by administering an effective amount of a dry powder composition comprising fibrinogen, thrombin and trehalose, or isomers or salts thereof, to exposed or separated tissues during the surgical procedure, wherein the dry powder composition contains about 0.5 to 20% w/w fibrinogen and about 25 to 1000 IU/g thrombin.

2. The method according to claim 1, wherein the dry powder composition comprises a mixture of first microparticles that comprise fibrinogen and second microparticles that comprise thrombin.

3. The method according to claim 1 wherein the dry powder composition contains about 0.5 to 20% w/w fibrinogen and about 100 to 500 IU/g thrombin.

4. The method according to claim 1 wherein the trehalose, isomer or salt thereof is selected from or more of hydrated crystalline trehalose, anhydrous crystalline trehalose, anhydrous amorphous trehalose, α,α-trehalose, α,β-trehalose (neo-trehalose), β,β-trehalose (iso-trehalose), or a mixture thereof.

5. The method according to claim 1, wherein the dry powder composition comprises a mixture of first microparticles that comprise fibrinogen and second microparticles that comprise thrombin, and wherein said first microparticles contain 0.5 to 20% w/w fibrinogen and wherein said second microparticles comprise 25 to 1000 IU/g thrombin.

6. The method as claimed in claim 1, wherein the dry powder composition further comprises 0.001 to 95% w/w of additive material, by weight of the composition.

7. The method according to claim 6, wherein the additive material comprises a biocompatible, water-absorbent material.

8. The method according to claim 6, wherein the additive material comprises a biocompatible, water-swellable material.

9. The method according to claim 6, wherein the additive material comprises a biocompatible, water-insoluble material.

10. The method according to claim 6, wherein the additive material comprises a polysaccharide.

11. The method according to claim 6, wherein the additive material has an average particle size of from about 10 nm to 1000 um.

12. The method as claimed in claim 11, wherein the average particle size is from about 10 to 500 um.

* * * * *